(12) United States Patent
Xu et al.

(10) Patent No.: US 9,195,042 B2
(45) Date of Patent: Nov. 24, 2015

(54) LASER BASED APPARATUS, METHODS AND APPLICATIONS

(71) Applicant: CORNELL UNIVERSITY, Ithaca, NY (US)

(72) Inventors: Chunhui (Chris) Xu, Ithaca, NY (US); Ke Wang, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 70 days.

(21) Appl. No.: 14/348,748

(22) PCT Filed: Oct. 1, 2012

(86) PCT No.: PCT/US2012/058244
§ 371 (c)(1),
(2) Date: Mar. 31, 2014

(87) PCT Pub. No.: WO2013/049793
PCT Pub. Date: Apr. 4, 2013

(65) Prior Publication Data
US 2014/0240702 A1     Aug. 28, 2014

Related U.S. Application Data

(60) Provisional application No. 61/541,322, filed on Sep. 30, 2011.

(51) Int. Cl.
*G01J 3/44* (2006.01)
*G02B 21/06* (2006.01)
*G01N 21/65* (2006.01)

(52) U.S. Cl.
CPC .......... *G02B 21/06* (2013.01); *G01N 21/65* (2013.01); *G01N 2021/653* (2013.01)

(58) Field of Classification Search
CPC ....... G01N 21/64; G01N 21/65; G01N 21/68; G01N 21/658; G01N 2021/656; G01J 3/02; G01J 3/44
USPC .............................................. 356/301, 72–73
See application file for complete search history.

(56) References Cited

U.S. PATENT DOCUMENTS

| | | | |
|---|---|---|---|
| 7,256,885 B2 | 8/2007 | Silberberg et al. | |
| 7,936,453 B2 | 5/2011 | Logan, Jr. et al. | |
| 2007/0013995 A1* | 1/2007 | Kaertner et al. | 359/330 |
| 2011/0273768 A1* | 11/2011 | Krishnamachari et al. | 359/388 |

OTHER PUBLICATIONS

Wang, Ke et al., Synchronized time-lens source for coherent Raman scattering microscopy, Nov. 8, 2010 / vol. 18, No. 23 / Optics Express 24019-24023.
Wang, Ke et al., Wavelength-tunable high-energy soliton pulse generation from a large-mode-area fiber pumped by a time-lens source, Optics Letters, vol. 36, Issue 6, pp. 942-944 (2011).

* cited by examiner

*Primary Examiner* — Abdullahi Nur
(74) *Attorney, Agent, or Firm* — William Greener; Bond, Schoeneck & King, PLLC (57) ABSTRACT

Embodied is a two-color, fiber-delivered picosecond source for coherent Raman scattering (CRS) imaging. A wavelength tunable picosecond pump is generated by nonlinear spectral compression of a prechirped femtosecond pulse from a mode-locked titanium:sapphire (Ti:S) laser. A 1064-nm picosecond Stokes pulse is generated by an all-fiber time-lens source (or suitable alternative source) that is synchronized to the Ti:S laser. The pump and Stokes beams are combined in an optical fiber coupler, which serves not only as the delivery fiber but also as the nonlinear medium for spectral compression of the femtosecond pulse. CRS imaging of mouse skin is performed to demonstrate the practicality of this source.

17 Claims, 5 Drawing Sheets

LASER BASED APPARATUS, METHODS AND APPLICATIONS

CROSS-REFERENCE TO RELATED APPLICATION

This application is related to, and derives priority from, U.S. Provisional Patent Application Ser. No. 61/541,322, filed 30 Sep. 2011, and titled Laser Based Apparatus, Method and Applications, the content of which is incorporated herein fully be reference.

STATEMENT OF GOVERNMENT INTEREST

The research that lead to the embodiments as disclosed herein, and the invention as claimed herein, was funded with United States Government support under Grant Number R21RR032392 awarded by the National Institutes of Health. The United States Government has rights in the invention as claimed herein.

BACKGROUND

Coherent Raman scattering (CRS) microscopy, with contrast from coherent anti-Stokes Raman scattering (CARS) or stimulated Raman scattering (SRS), allows label-free imaging of biological samples with endogenous image contrast based on vibrational spectroscopy. An important technical challenge in CRS microscopy is the requirement of two synchronized picosecond excitation sources. Thus, desirable are CRS microscopy apparatus, CRS microscopy systems and CRS microscopy methods that provide novel and efficient means to provide two synchronized picosecond excitation sources.

SUMMARY

Generally, embodiments may include fiber-delivered two-color picosecond sources for CARS imaging. In a particular embodiment, an 817-nm pump pulse is generated by nonlinear spectral compression of a negatively prechirped pulse from a femtosecond Ti:S (i.e., titanium:sapphire) laser in a 2×2 fiber coupler. In the presence of self-phase modulation and negative prechirping, the spectrum of the pulse can be compressed by nonlinear propagation in an optical fiber. Such a nonlinear spectral compression process retains the optical power in the original pulse, in contrast with spectral filtering. In the particular embodiment, a 7.6 nm spectral bandwidth of the femtosecond Ti:S output is compressed to 0.68 nm, which is well-suited for CRS imaging.

Prechirping of the pulse is accomplished through a rotating cylindrical lens system, which offers tunable dispersion with spatial beam stability, a desirable feature for coupling light into fibers. A 1064-nm Stokes pulse is generated by a synchronized, all-fiber time-lens source, and also propagates through the 2×2 fiber coupler. This particular embodiment provides for CARS imaging of mouse skin at a $CH_2$ stretching frequency (2845 $cm^{-1}$) to demonstrate the practicality of the two-color picosecond source.

Thus, this particular embodiment describes an apparatus for coherent anti-Stokes Raman spectroscopy comprising a femtosecond Ti:S laser, a prechirping system, a fiber coupler, and an all-fiber time-lens source synchronized with the femtosecond Ti:S laser and coupled to the fiber coupler. Also described within the context of the forgoing apparatus in accordance with the particular embodiment is a method for coherent anti-Stokes Raman spectroscopy imaging comprising: (1) generating a wavelength tunable picosecond pump by nonlinear spectral compression of a prechirped femtosecond pulse from a mode-locked titanium:sapphire laser; (2) generating a picosecond Stokes pulse using an all-fiber time-lens source that is synchronized to the titanium:sapphire laser; (3) combining the pump and Stokes beams in an optical fiber coupler; (4) delivering the combined beams to a sample; and (5) collecting the Raman signal.

A particular optical apparatus in accordance with the embodiments includes a first laser source that provides a first laser output through a first laser output port. This particular optical apparatus also includes a prechirping apparatus optically coupled to the first laser output port to provide a prechirped first laser output from the first laser output. This particular optical apparatus also includes a second light source synchronized with the first laser source and having a second light output that is optically coupled (i.e., combined) with the prechirped first laser output, where the second light source is selected from the group consisting of: (1) a second laser source different than the first laser source; and (2) a time-lens source.

Another particular optical apparatus in accordance with the embodiments includes a laser source that provides a laser output through a laser output port. This other particular optical apparatus also includes a prechirping apparatus optically coupled to the laser output port to provide a prechirped laser output from the laser output. This other particular optical apparatus also includes a time-lens source synchronized with the laser source and having a time-lens output that is optically coupled (i.e., combined) with the prechirped laser output.

Another particular optical apparatus in accordance with the embodiments includes a titanium:sapphire femtosecond laser source that provides a laser output through a laser output port. This other particular optical apparatus also includes a prechirping apparatus optically coupled to the laser output port to provide a prechirped laser output from the laser output. This other particular optical apparatus also includes an all-fiber time-lens source synchronized with the titanium:sapphire laser source and having a time-lens output that is optically coupled (i.e., combined) with the prechirped laser output.

A particular imaging method in accordance with the embodiments includes providing an imaging apparatus comprising: (1) a laser source that provides a laser output through a laser output port; (2) a prechirping apparatus optically coupled to the laser output port to provide a prechirped laser output from the laser output; (3) a time-lens source synchronized with the laser source and having a time-lens output that is optically coupled (i.e., combined) with the prechirped laser output; and (4) a microscope coupled with the time-lens output and the prechirped laser output (i.e., as a specimen illumination source). This particular imaging method also includes energizing the laser source and the time-lens source while imaging (i.e., Raman imaging) a specimen while using the microscope.

Another particular imaging method in accordance with the embodiments includes generating a wavelength tunable picosecond pump by nonlinear spectral compression of a prechirped femtosecond pulse from a mode-locked titanium:sapphire laser. This other particular imaging method also includes generating a picosecond Stokes pulse using an all-fiber time-lens source that is synchronized to the titanium:sapphire laser. This other particular imaging method also includes combining the pump and Stokes beams in an optical fiber coupler. This other particular imaging method also includes delivering the combined beams to a sample. This other particular imaging method also includes collecting a Raman signal from the sample.

BRIEF DESCRIPTION OF THE DRAWINGS

The objects, features and advantages of the embodiments are understood within the context of the Detailed Description of the Embodiments, as set forth below. The Detailed Description of the Embodiments is understood within the context of the accompanying drawings, that form a material part of this disclosure, wherein:

FIG. 1 shows an experimental configuration of a of a fiber-delivered two-color picosecond source for CARS imaging in accordance with a first embodiment. A 1064-nm synchronized all-fiber time-lens source is described in detail in Wang et al., "Synchronized time-lens source for coherent Raman scattering microscopy," Opt. Express 18, 24019-24024 (2010), and is incorporated herein fully by reference. M: mirror, G: 1800 line/mm grating, L1: f=30 cm concave lens, CL: f=10 m concave cylindrical lens, BS: beam splitter, HWP: half-wave plate, QWP: quarter-wave plate, L2: aspheric lens, CFBG: chirped fiber Bragg grating, L3: collimating lens, LPF: 800 nm long pass filter, PC: polarization controller.

FIG. 5 shows an experimental configuration of a fiber-delivered two-color picosecond source for CARS imaging in accordance with a second embodiment. M: mirror, G: 1800 line/mm grating, L1:f=30 cm collimating lens, CL: f=10 m concave cylindrical lens, BS: beam splitter, HWP: half-wave plate, QWP: quarter-wave plate, L2: aspheric lens, CFBG: chirped fiber Bragg grating, L3: collimating lens, LPF: 800 nm long pass filter, PC: polarization controller, BB: broadband, MZ: Mach-Zehnder intensity modulator. Electrical paths are labeled with dashed lines, and optical paths are labeled with solid lines.

DETAILED DESCRIPTION OF THE EMBODIMENTS

In the following description, reference is made to the accompanying drawings that form a part of this specification, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

1. First Embodiment

A first embodiment is directed towards a fiber-delivered two-color picosecond source for CARS imaging. An 817-nm pump pulse is generated by nonlinear spectral compression of a negatively prechirped pulse from a femtosecond Ti:S laser in a 2×2 fiber coupler. In the presence of self-phase modulation and negative prechirping, the spectrum of the pulse can be compressed by nonlinear propagation in an optical fiber. Such a nonlinear spectral compression process retains the optical power in the original pulse, in contrast to spectral filtering. Experimentally within the context of the first embodiment, a 7.6 nm spectral bandwidth of a femtosecond Ti:S output is compressed to 0.68 nm, which is well-suited for CRS imaging. Prechirping of the pulse is accomplished through a rotating cylindrical lens system, which offers tunable dispersion with spatial beam stability, a desirable feature for coupling light into fibers. A 1064-nm Stokes pulse is generated by a synchronized, all-fiber time-lens source, and also propagates through the 2×2 fiber coupler. The first embodiment describes CARS imaging of mouse skin at the $CH_2$ stretching frequency (2845 $cm^{-1}$) to demonstrate the practicality of the two-color picoseconds source in accordance with the embodiments.

Figure 1:
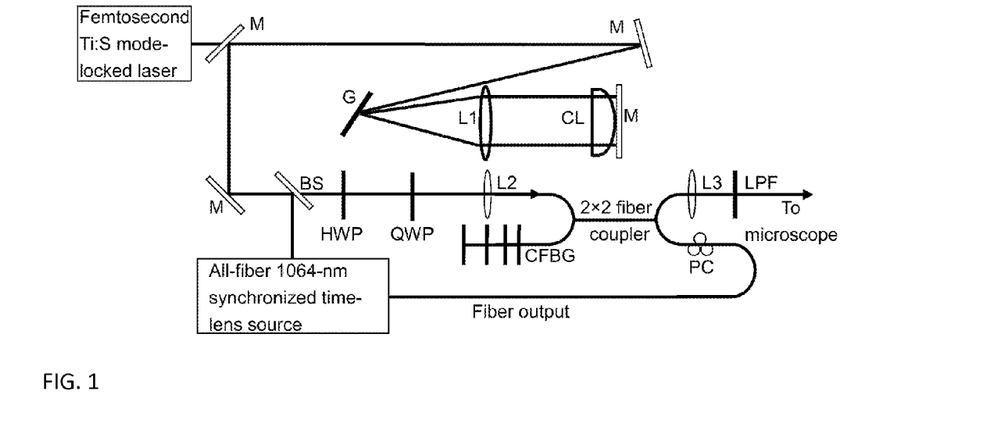

In an experimental execution of the first embodiment as illustrated in FIG. 1, 817-nm femtosecond pulses are generated from a mode-locked Ti:S laser (Tsunami, Spectra-Physics). The prechirp of the femtosecond pulse is provided by a rotating cylindrical lens system in a 4f configuration, which consists of an 1800 lines/mm silver coated grating, a f=30 cm spherical lens, a f=10 cm concave cylindrical lens (SCX-50.8-5000.0-C, CVI Melles Griot) and a mirror. The cylindrical lens is mounted on a rotation stage for rotation in the plane perpendicular to the direction of light propagation. In this particular experimental embodiment of the first embodiment, for an incident angle of 44° onto the grating, the calculated maximum anomalous dispersion is $-1.4 \times 10e5$ $fs^2$. The prechirped 817-nm pulse is coupled into a 2×2 fiber coupler (FC1064-50B-FC, Thorlabs) for nonlinear spectral compression and fiber-optic beam combining. The total propagation length of the 817-nm pump pulse in the fiber is 107 cm. A half-wave plate and a quarter-wave plate are inserted before the coupling lens, to adjust the polarization of the output pump pulse after the fiber. The 1064-nm Stokes pulse is generated by an all-fiber time-lens source synchronized to the Ti:S laser, which is described in detail in Wang et al., "Synchronized time-lens source for coherent Raman scattering microscopy," Opt. Express 18, 24019-24024 (2010), and which is incorporated herein fully by reference. The RF signal for synchronization is provided by a high-speed photodiode that samples the 80-MHz Ti:S optical pulse train. A chirped fiber Bragg grating (CFBG) spliced to the fiber coupler (instead of a circulator as in the foregoing reference), was used as an all-fiber dispersion compensator for the time-lens source. A polarization controller (PC) is used to adjust the polarization of the 1064-nm output from the fiber coupler, ensuring that the Stokes pulse is linearly polarized and parallel to that of the pump to maximize CARS signal. A discrete RF delay (PDL-10A, Colby Instruments) and a continuously tunable RF delay provide a large tuning range (0.795 ns) to adjust the relative time delay between the pump and the Stokes pulses without any mechanical optical delay line. The 2×2 fiber coupler acts as a spatial beam combiner and delivery fiber for both the pump and the Stokes pulses, ensuring perfect spatial overlap of the two beams for CRS imaging. After collimation and an 800-nm long-pass filter (LPF), which removes the four-wave mixing background generated in the fiber coupler, the spatially and temporally overlapping pump and Stokes pulses are sent into a microscope (described in detail in Balu et al, "Fiber delivered probe for efficient CARS imaging of tissues," Opt. Express 18, 2380-2388 (2010), and incorporated herein fully by reference), for CARS imaging. The CARS signal is excited and collected in the epi-direction with a water immersion objective lens (XLUMPlanFl, Olympus, NA=0.95).

Figure 2:
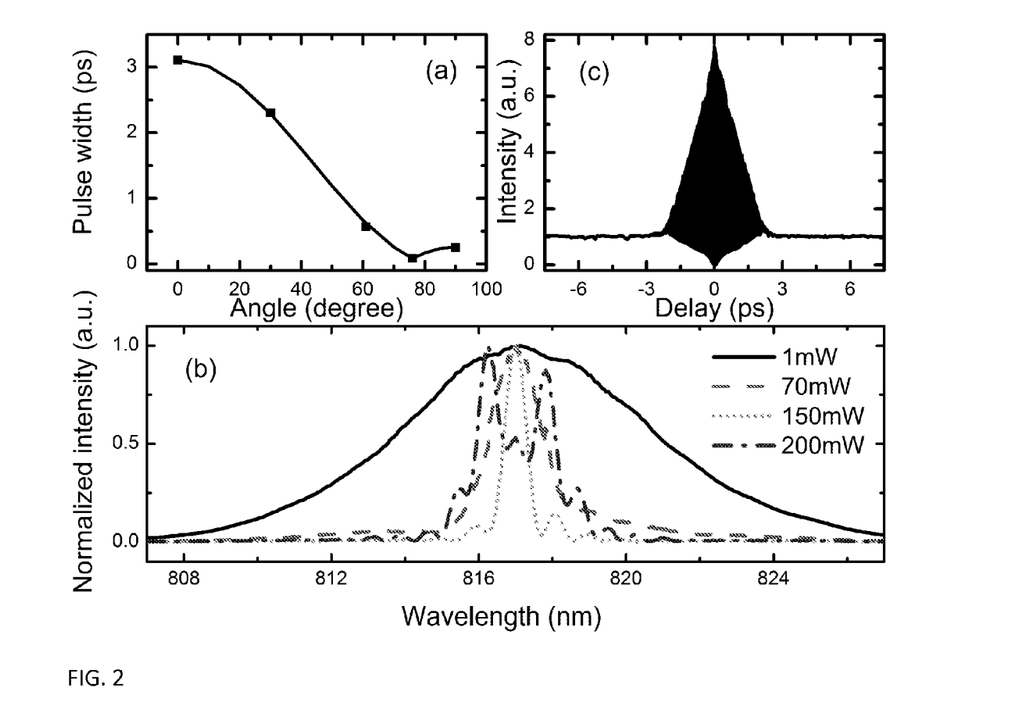
FIG. 2 shows for the first embodiment: (a) Measured (dots) and calculated (line) pulse width as a function of rotation angle of a cylindrical lens. (b) Measured 817-nm pump pulse spectra at various output powers from a fiber coupler. (c) Measured second-order interferometric autocorrelation trace at 150 mW output power.

In accordance with the foregoing experimentally embodied apparatus, one may characterize a linear dispersion of the rotating cylindrical lens system before the fiber coupler. The pulse width as a function of the rotation angle of the cylindrical lens is measured [dots in FIG. 2(a)], and compared with theoretical calculation [solid line in FIG. 2(a)] by assuming the maximum dispersion of $-1.4 \times 10e5$ $fs^2$ at 0°. Experimental and theoretical results agree well. Note that as the angle decreases (dispersion increases), the pulse width is compressed to its minimum at 76° due to other dispersive elements in the beam path (e.g., an optical isolator) before the cylindrical lens system. To maximize the power that can be spectrally compressed, the cylindrical lens is fixed at maximum dispersion (0°). The measured spectra of the 817-nm pulse as a function of the output power from the fiber coupler are shown in FIG. 2(b). As power increases, the spectrum is progressively compressed, and reaches its minimum of 0.68 nm at 150 mW output power [dotted line in FIG. 2(b)]. This corresponds to 11.2 times spectral compression from that of linear propagation at low power [solid line in FIG. 2(b)]. As the output power further increases, the spectrum broadens again [dash-dotted line in FIG. 2(b)] due to the maximum prechirp provided by the current system, which may be further increased by using a shorter focal length cylindrical lens. The pulse width at maximum spectral compression (i.e., at 150 mW output), deconvolved from the measured second-order interferometric autocorrelation trace [FIG. 2(c)], is 1.8 ps.

Figure 3:
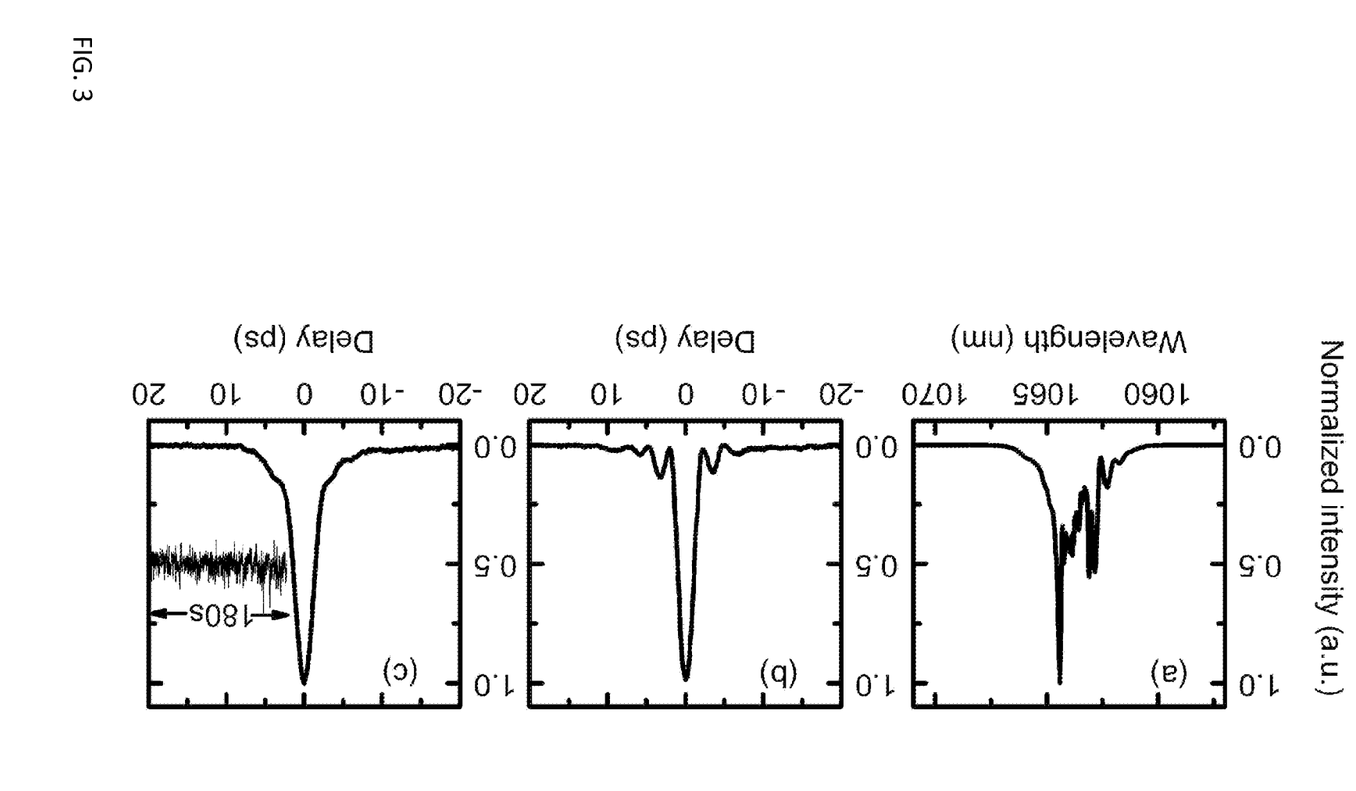
FIG. 3 shows for the first embodiment: (a) Measured spectrum of a time-lens output. Cross correlation traces of the time-lens output with an 87-fs pulse. (b) and the 150-mW, 1.8-ps pulse from the fiber coupler (c). Inset in (c) shows the measured sum-frequency signal at the half maximum of the cross-correlation trace over 180 seconds.

One may then characterize the time-lens output and the synchronization performance. The measured spectral bandwidth (FWHM) is 1.7 nm [FIG. 3(a)]. For temporal profile characterization, one may measure the cross correlation between the time-lens output and the 87-fs pulse directly from the Ti:S laser, using sum-frequency (SF) generation in a BBO crystal. The relative delay between the pulses is readily scanned by tuning the electronic RF delay line. FIG. 3(b) shows that the pulse width of the time-lens output is 2.2 ps. The cross correlation between the time-lens output and the 1.8-ps spectrally compressed 817-nm pulse is shown in FIG. 3(c). The FWHM is 2.9 ps. To measure the relative timing jitter between the pump and Stokes pulses, one may record an SF intensity fluctuation at half maximum of the cross correlation trace [inset in FIG. 3(c)]. The RMS timing jitter over a measurement time of 180 seconds is 110 fs, only a small fraction of the pulse widths. The measured output power of the 1064-nm Stokes pulse is 110 mW.

Figure 4:
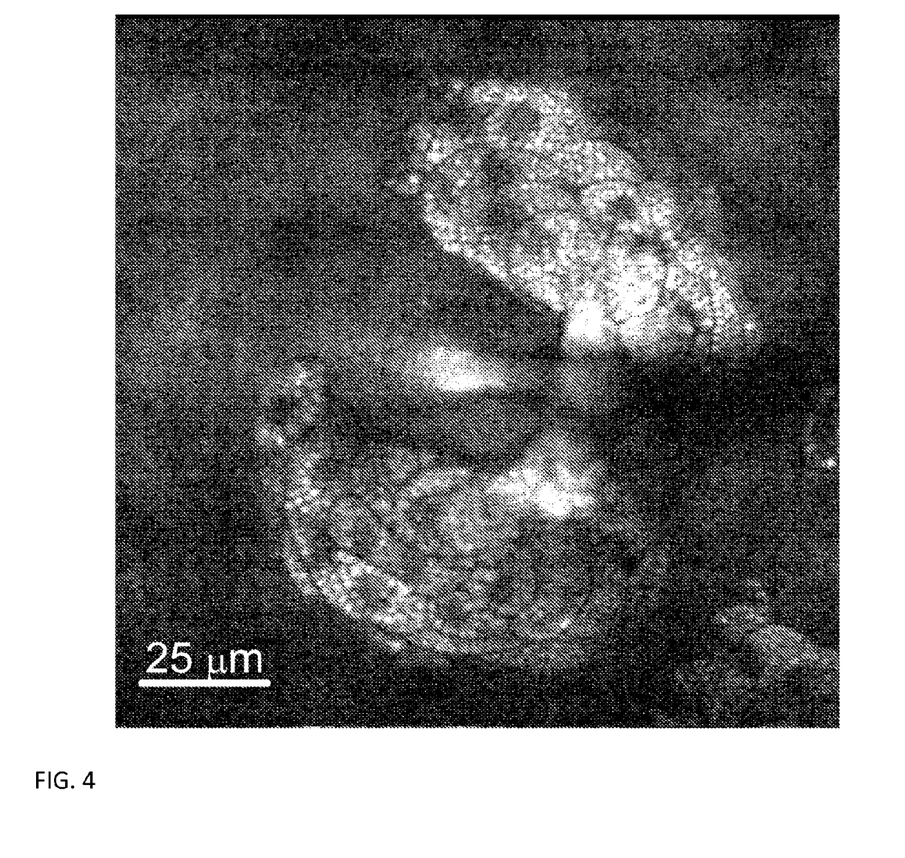
FIG. 4 shows for the first embodiment a CARS image of sebaceous glands at the $CH_2$ stretching frequency in a mouse ear. 512×512 pixels, 4 s/frame, no average.

One may perform CARS imaging of sebaceous glands at the $CH_2$ stretching frequency in ex vivo mouse ear. FIG. 4 highlights the practicality of the two-color, fiber-delivered picosecond source for CARS imaging. While CRS imaging of the $CH_2$ bond is demonstrated, the wavelength tunability of the femtosecond Ti:S laser ensures that a wide range of stretching bands can be covered by the two-color source.

In conclusion, the particular foregoing first embodiment demonstrates a fiber-delivered two-color, picosecond source for CARS imaging. A 2×2 fiber coupler spectrally compresses a pump pulse from a mode-locked femtosecond laser, and spatially combines the pump and the Stokes pulses, the latter of which is generated by a synchronized, all-fiber time-lens source. The temporal overlap of the two pulses is electronically adjusted without any mechanical optical delay line, greatly facilitating the temporal alignment of the excitation beams for CRS imaging. Mouse skin imaging at $CH_2$ stretching frequency (2845 $cm^{-1}$) is performed to demonstrate the practicality of this source. The combination of the all-fiber time-lens source and the nonlinear spectral compression of a femtosecond source in an optical fiber has the potential to make CRS imaging easily accessible to any researcher with a wavelength tunable femtosecond source.

2. Second Embodiment

Figure 5:
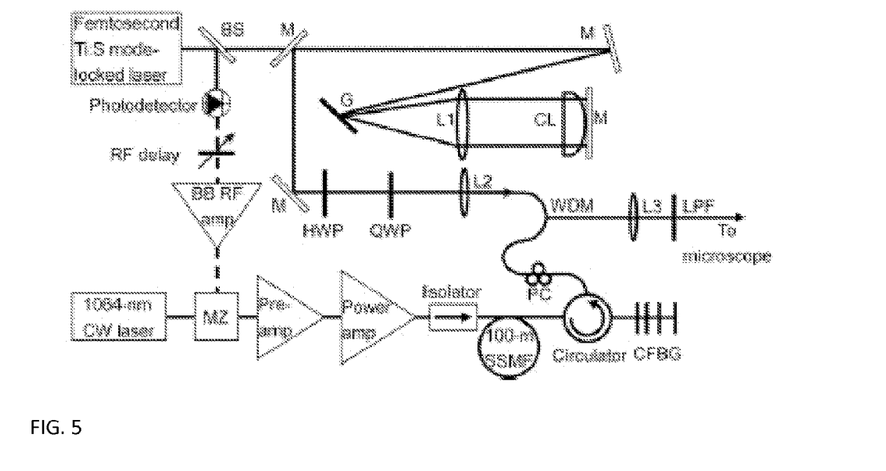

In a second embodiment as illustrated in FIG. 5, 80-MHz, 90-fs pump pulses centered at 817-nm are generated from a mode-locked Ti:S laser (Tsunami, Spectra-Physics). The pre-chirp of the femtosecond pulse is provided by a rotating cylindrical lens system in a 4f configuration, which provides tunable anomalous dispersion up to $-1.4 \times 10e5$ $fs^2$. The pre-chirped 817-nm pulse is coupled into a WDM for nonlinear spectral compression, fiber-optic beam combining, and delivery. To generate a 1064-nm Stokes pulse, a fast GaAs photo-detector (ET-4000, 10 GHz, EOT) converts the 80-MHz pump pulse train into a synchronized RF pulse train, which is amplified by broadband RF amplifiers and used to drive the MZ intensity modulator. The intensity modulator carves a synchronized 80-MHz, 55-ps optical pulse train from a 1064-nm CW laser (QFBGLD-1060-30PM, QPhotonics). The preamp and the power amplifier boost the energy of the optical pulse for nonlinear spectral broadening in 100-m SSMF, which replaces the phase modulators in the time-lens setup. For dispersion compensation, the spectrally broadened 1064-nm pulse is compressed with an all-fiber dispersion compressor consisting of a circulator and a chirped fiber Bragg grating. The output port of the compressor is spliced to the fiber WDM. In the experimental configuration in accordance with the second embodiment, the fiber WDM serves three purposes: (1) combining the pump and the Stokes beams spatially; (2) nonlinear spectral compression of the pump; and (3) fiber delivery of both beams. An in-line fiber polarization controller before the WDM adjusts the polarization of the 1064-nm output, ensuring that the Stokes beam is linearly polarized and parallel to that of the pump to maximize the CARS signal. An electronic discrete RF delay (PDL-10A, Colby Instruments) and a continuously tunable RF delay provide a large tuning range (0.795 ns) to adjust the relative time delay between the pump and the Stokes pulses without any mechanical optical delay line. After collimation and an 800-nm long-pass filter (LPF), which removes the four-wave mixing background generated in the fiber coupler, the spatially and temporally overlapping pump and Stokes pulses are sent into a microscope, as described in detail in Kobat et al., Opt. Express 17, 13354 (2009), which is incorporated herein fully by reference, for CARS imaging. CARS signal is excited and collected in the epi-direction with a water immersion objective lens (XLUMPlanFl, Olympus, NA=0.95) and detected by a GaAsP photomultiplier tube (PMT).

Figure 6:
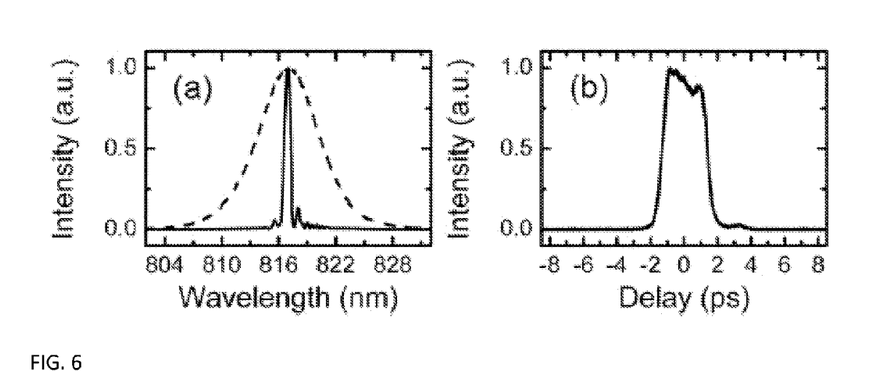
FIG. 6 shows for the second embodiment: (a) Measured 817-nm pump spectra from the WDM at linear propagation (dashed line) and maximum spectral compression (solid line). (b) Cross correlation trace between the 90-fs and the spectrally compressed 817 nm pulses.

One may first characterize the 817-nm pump pulse. Spectral compression of a negatively prechirped femtosecond pulse due to SPM in optical fibers is explained in detail in Wang et al., Opt. Lett. 36, 4233 (2011). At maximum group delay dispersion ($-1.4\times10e5$ fs$^2$) and an output power of 145 mW from the WDM, the full-width-at-half-maximum (FWHM) bandwidth of the pump spectrum is compressed to its minimum, from 7.4 nm to 0.72 nm [FIG. 6(a)] with a spectral compression ratio of 10.3. To obtain the temporal profile of the spectrally compressed pump pulse, one may measure cross correlation trace between the 90-fs 817-nm pulse and the spectrally compressed pump pulse, through background-free noncollinear sum-frequency (SF) generation in a barium borate (BBO) crystal, shown in FIG. 6(b). The measured FWHM pulse width is 2.7 ps.

Figure 7:
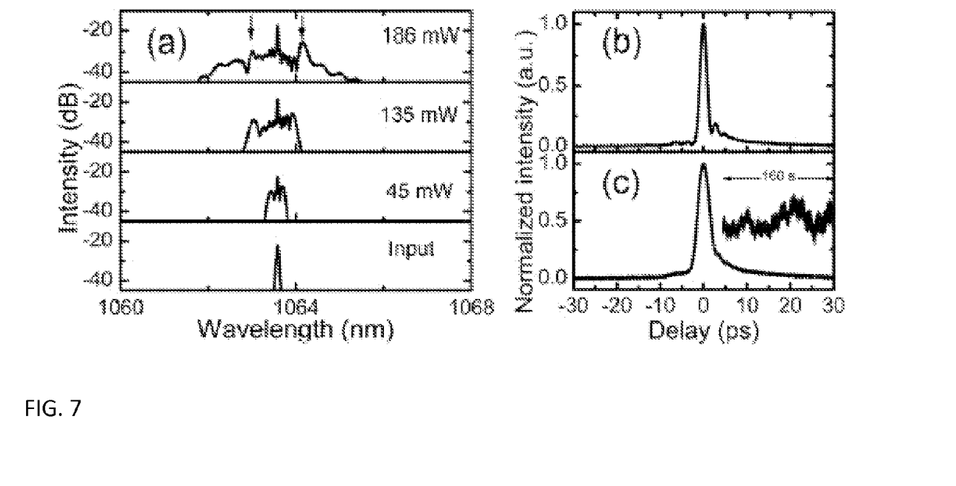
FIG. 7 shows for the second embodiment: (a) The measured 1064-nm pulse spectra at various output power from the WDM. Cross correlation trace between the 186-mW 1064-nm pulse with the 90-fs 817-nm pulse from the Ti:S laser (b) and the spectrally compressed 2.7-ps 817-nm pump pulse (c). Inset in (c) shows the measured sum-frequency signal at the half maximum of the cross-correlation trace over 160 s.

One may then characterize the 1064-nm Stokes pulse and the synchronization performance. As power increases, the 1064-nm spectrum continuously broadens due to SPM [FIG. 7(a)]. At the maximum output power of 186 mW from the WDM (820 mW output from the 100-m SSMF), the measured bandwidth [defined by the two outmost peaks indicated by the arrows FIG. 7(a)] is 1.14 nm. To determine the temporal profile, one may measure the cross correlation between the 1064-nm Stokes pulse and the 90-fs 817-nm pulse directly from the Ti:S laser [FIG. 7(b)]. To characterize the timing jitter, cross correlation of the Stokes pulse and the 2.7-ps spectrally compressed 817-nm pump pulse is performed [FIG. 7(c)]. All cross correlation measurements use SF generation in the BBO crystal. A bandpass filter placed before the photodiode removes the residual second harmonic of the 817-nm pulse and the 1064-nm Stokes pulse, which guarantees background-free SF measurement in the collinear configuration. The relative delay between the pulses is readily scanned by tuning the electronic RF delay line, instead of a mechanical delay line used for FIG. 6(b). FIG. 7(b) shows that the FWHM pulse width of the compressed 1064-nm pulse is 1.9 ps. The FWHM of the cross correlation between the 1064-nm pulse and the 2.7-ps spectrally compressed 817-nm pulse is 3.3 ps. To measure the relative timing jitter between the pump and Stokes pulses, one may record the SF intensity fluctuation at half maximum of the cross correlation trace [inset in FIG. 7(c)]. The RMS timing jitter over a measurement time of 160 s is 180 fs, only a small fraction of the pulse widths.

Figure 8:
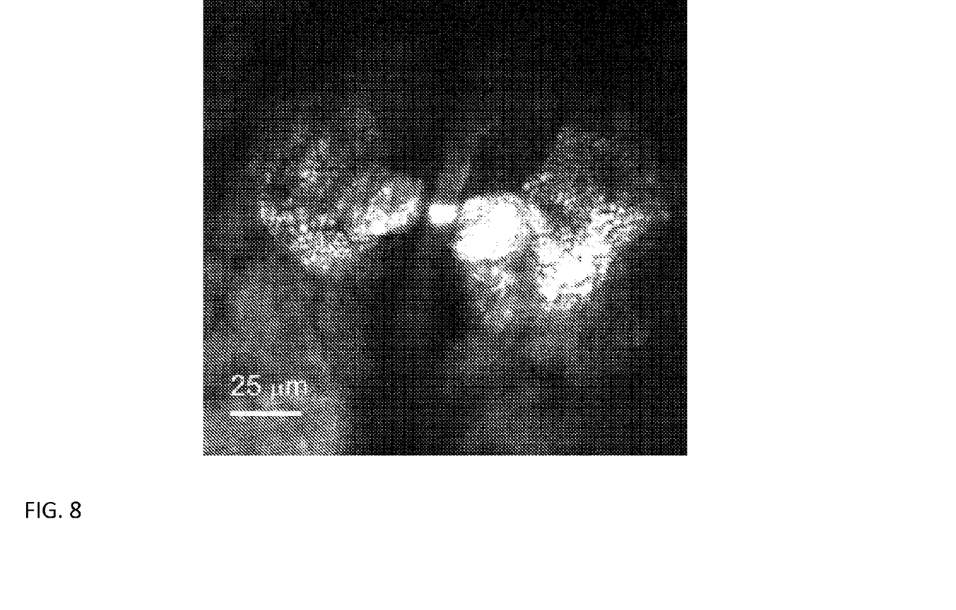
FIG. 8 shows for the second embodiment a CARS image of sebaceous glands at the $CH_2$ stretching frequency in mouse ear. 512×512 pixels, 4 s/frame, no average.

With this fiber-delivered two-color source in accordance with the second embodiment, one may perform CARS imaging of sebaceous glands at the $CH_2$ stretching frequency (2845 cm$^{-1}$) in ex vivo mouse ear. FIG. 8 highlights the practicality of the two-color, fiber-delivered picosecond source for CARS imaging. While CRS imaging of the $CH_2$ bond is demonstrated, the wavelength tunability of the femtosecond Ti:S laser, together with proper adjustment of the grating angle and choice of fast photodetectors responsive to the pump wavelength, ensures that a wide range of stretching bands can be covered by the two-color source. For example, tuning the pump wavelength to 909 nm, one may demonstrate CRS imaging of drug delivery in mouse skin at a polyene stretching frequency (1600 cm$^{-1}$).

Compared with the time-lens source in accordance with the first embodiment Stokes pulse generation through nonlinear spectral broadening in accordance with the second embodiment is simpler and more cost effective to implement. High speed phase modulators and relevant RF filter and amplifiers are no longer needed, eliminating the major cost of the time-lens system. On the other hand, the timing jitter described herein is larger than that of the time-lens source, and there is some polarization instability over a long imaging session of several hours. One may attribute these to the long SSMF (100 m) that was used. A long fiber is more susceptible to environmental variations such as temperature fluctuations and mechanical vibrations.

In conclusion, demonstrated herein in accordance with a second embodiment is a fiber-delivered two-color, picosecond source for CARS imaging through nonlinear spectral transformation. The pump pulse is generated through nonlinear spectral compression of a prechirped femtosecond pulse, while the Stokes pulse is generated through SPM-induced spectral broadening of a 55-ps pulse and subsequent dispersive compression. Spectral compression of the femtosecond pump pulse, beam combining, and fiber delivery are readily accomplished in a fiber WDM. The temporal overlap of the two pulses is electronically adjusted without any mechanical optical delay line, greatly facilitating the temporal alignment of the excitation beams for CRS imaging. Mouse skin imaging at $CH_2$ stretching frequency is performed to demonstrate the practicality of this source. The nonlinear spectral broadening scheme of the Stokes pulse replaces phase modulation with phase modulators in the time-lens source, which potentially reduces the complexity and cost of the Stokes source for CRS imaging.

All references, including publications, patent applications, and patents cited herein are hereby incorporated by reference in their entireties to the extent allowed, and as if each reference was individually and specifically indicated to be incorporated by reference and was set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein is merely intended to serve as a shorthand method of referring individually to each separate value falling within the range, unless otherwise indicated herein, and each separate value is incorporated into the specification as if it was individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. An optical apparatus comprising:
   a wavelength-tunable laser source that provides a pump beam output having a femtosecond pulse duration at a first desired wavelength through an output port of the pump beam laser source;
   a prechirping apparatus optically coupled to the output port to provide a prechirped the femtosecond pump beam output at the first desired wavelength;
   a light source assembly comprising at least one of a different laser source and a time-lense source having a Stokes pulse output having a picosecond pulse duration at a second desired wavelength that is different than the first desired wavelength; and
   a fiber optic coupler having an input port optically coupled to both the prechirped femtosecond pump beam output at the first desired wavelength and the picosecond Stokes pulse output at the second desired wavelength, and having an optical output characterized by a spatially-overlapping, non-linearly-spectrally compressed pump beam output having a picosecond pulse duration and the Stokes picosecond pulse output.

2. The optical apparatus of claim 1 wherein the pump beam laser source comprises a Ti:S mode-locked laser source.

3. The optical apparatus of claim 1 wherein the different laser source comprises a continuous wave laser source.

4. The optical apparatus of claim 1 wherein the time-lens source comprises an all-fiber time-lens source.

5. The optical apparatus of claim 1 wherein the coupler comprises a 2×2 fiber coupler.

6. The optical apparatus of claim 1 further comprising a microscope optically coupled to the spatially-overlapping, wavelength-tunable, non-linearly-spectrally compressed pump beam output having a picosecond pulse duration and the Stokes picosecond pulse output.

7. The optical apparatus of claim 1 wherein:
   the first desired wavelength is 817 nanometers (nm); and
   the second desired wavelength is 1064 nm.

8. The apparatus of claim 1, wherein the fiber optic coupler is a 2×2 coupler.

9. The apparatus of claim 1, wherein the fiber optic coupler is a wavelength division multiplexer (WDM).

10. The apparatus of claim 1, wherein the prechirped the first laser femtosecond pump beam output is negatively prechirped.

11. An imaging method comprising:
    generating a prechirped laser pump beam having a femtosecond pulse duration at first desired wavelength;
    generating a Stokes pulse output having a picosecond pulse duration at a second desired wavelength that is different than the first desired wavelength;
    inputting the prechirped femtosecond laser pump beam to a fiber optic coupler to obtain an nonlinearly spectrally compressed, picosecond duration laser pump beam in the fiber optic coupler;
    inputting the Stokes picosecond pulse output in the fiber optic coupler to spatially overlap the picosecond duration, nonlinearly spectrally compressed laser pump beam and the Stokes picosecond pulse output;
    inputting the spatially-overlapped, non-linearly-spectrally compressed, picosecond duration pump beam output and the Stokes picosecond pulse output from the fiber optic coupler to a microscope; and
    illuminating a sample to be imaged with the spatially-overlapped, non-linearly-spectrally compressed, picosecond duration pump beam output and the Stokes picosecond pulse output.

12. The method of claim 11 wherein the sample comprises a biological specimen.

13. The method of claim 11, further comprising collecting a Raman signal from the sample.

14. The method of claim 11, further comprising providing a 2×2 fiber coupler for nonlinearly spectrally compressing the negatively prechirped laser pump beam.

15. The method of claim 11, further comprising providing a fiber wavelength division multiplexer (WDM) for nonlinearly spectrally compressing the prechirped laser pump beam.

16. The method of claim 11, further comprising generating a negatively prechirped laser pump beam having a femtosecond pulse duration at a first desired wavelength.

17. The method of claim 11, further comprising temporally overlapping the non-linearly-spectrally compressed, picosecond duration pump beam output and the Stokes picosecond pulse output.

* * * * *